United States Patent [19]

Hindmarsh et al.

[11] Patent Number: 5,679,846
[45] Date of Patent: Oct. 21, 1997

[54] PROCESS FOR THE PRODUCTION OF TEREPHALIC ACID

[75] Inventors: Eric Hindmarsh, North Yorkshire; John Arthur Turner; Alan Macpherson Ure, both of Cleveland, all of England

[73] Assignee: Imperial Chemical Industries PLC, London, England

[21] Appl. No.: 682,424

[22] Filed: Jul. 17, 1996

Related U.S. Application Data

[63] Continuation of Ser. No. 470,955, Jun. 6, 1995, Pat. No. 5,563,293, which is a continuation of Ser. No. 847,735, Mar. 9, 1992.

Foreign Application Priority Data

Mar. 7, 1991 [GB] United Kingdom ............... 9104776

[51] Int. Cl.[6] .................................................. C07C 51/43
[52] U.S. Cl. ........................................................ 562/414
[58] Field of Search .................................. 562/413, 414, 562/485, 486

[56] References Cited

U.S. PATENT DOCUMENTS

| | | | |
|---|---|---|---|
| 4,038,193 | 7/1977 | Oosten . | |
| 4,782,181 | 11/1988 | James | 562/487 |
| 4,786,753 | 11/1988 | Partenheimer et al. | 562/416 |
| 4,939,297 | 7/1990 | Browder | 562/485 |
| 5,008,450 | 4/1991 | Yamamoto | 562/485 |
| 5,093,001 | 3/1992 | Ueda | 210/403 |
| 5,175,355 | 12/1992 | Streich | 562/485 |
| 5,200,557 | 4/1993 | Gee | 562/486 |

FOREIGN PATENT DOCUMENTS

| | | |
|---|---|---|
| 321272 | 3/1989 | European Pat. Off. . |
| 0406424 | 1/1991 | European Pat. Off. . |
| 0498591 | 8/1992 | European Pat. Off. . |
| 926605 | 4/1955 | Germany . |
| 970492 | 9/1964 | United Kingdom . |
| 1152575 | 5/1969 | United Kingdom . |
| WO9218453 | 10/1992 | WIPO . |
| WO9218454 | 10/1992 | WIPO . |

*Primary Examiner*—Samuel Barts
*Attorney, Agent, or Firm*—Cushman Darby & Cushman Intellectual Property Group of Pillsbury Madison & Sutro LLP

[57] ABSTRACT

A terephthalic acid slurry in acetic acid is produced by oxidizing p-xylene in acetic acid, removing water by evaporation of a stream of water and acetic acid, and returning acetic acid to the oxidation step. The terephthalic acid is separated from the reaction medium in a first zone to leave a deposit on a band, the deposit is washed with a first aqueous medium in a second zone, removed from the band in a third zone, and admixed with a second aqueous medium. Reaction medium is passed from the first zone to the oxidation step and terephthalic acid is recovered, preferably after further purification.

15 Claims, 2 Drawing Sheets

PROCESS FOR THE PRODUCTION OF TEREPHALIC ACID

This is a continuation of application Ser. No. 08/470,955, filed Jun. 6, 1995 now U.S. Pat. No. 5,563,293 which is a continuation of Ser. No. 07/847,735, filed Mar. 9, 1992.

This invention relates to a process for the production of terephthalic acid.

Terephthalic acid is produced commercially by oxidising para xylene with oxygen in a liquid phase which comprises acetic acid and a dissolved catalyst. The temperature of the reaction and the concentration of water, which is produced as a by-product, in the liquid phase is controlled by withdrawing from the reaction as vapour a stream comprising water and acetic acid. Water may be removed from at least part of the stream leaving a stream enriched in acetic acid which may be returned to the reaction.

The terephthalic acid product is obtained as a slurry of crystals of terephthalic acid in a liquid phase comprising acetic acid, any catalyst and impurities. The terephthalic acid may be separated from the liquid for example by centrifugation or filtration, washed with acetic acid, dried to remove acetic acid, dissolved in water at elevated temperature, hydrogenated to reduce organic impurities and recrystallised from the water to give a pure product.

This procedure requires drying, handling, storage and subsequent reslurrying of the crude terephthalic acid powder; all these operations involve special equipment and incur both capital and variable costs of operation. Furthermore, such a procedure allows catalyst residues and impurities to pass into the later stages of the process.

The present invention provides a significantly improved washing of the terephthalic acid in the reaction medium. The improved wash allows re-optimisation of the oxidation step such that higher impurity levels may be tolerated in the oxidation step whilst maintaining an acceptable terephthalic acid product purity.

This invention provides a process for the production of terephthalic acid comprising oxidising paraxylene in a reaction medium containing acetic acid to produce a slurry of terephthalic acid in the reaction medium; depositing the slurry on a moveable band of filter material; removing reaction medium from the slurry through said band in a first zone to produce a first wet deposit; moving said deposit on said band to a second zone in which it is washed with a first aqueous medium; removing the first aqueous medium and reaction medium present in said first wet deposit through said band to produce a second wet deposit; moving said second wet deposit to a third zone; removing said second wet deposit from said band in said third zone; admixing said second deposit, either whilst so removing it or subsequently, with a second aqueous medium, thereby producing a slurry of terephthalic acid in the second aqueous medium, recovering terephthalic acid from the second aqueous medium; recovering the reaction medium removed through the band in the first zone and recycling at least part of the reaction medium so recovered directly or indirectly to the oxidation step.

It is desirable that the second aqueous medium is substantially pure water in order to avoid adding impurities to the terephthalic acid product. Further, the terephthalic acid is preferably recovered after further purification desirably in a terephthalic acid purification plant.

In order to control the temperature and/or water content of the reaction, a mixture of acetic acid and water is suitably removed from the reaction medium in the oxidation step by evaporation, water is removed from at least part of the said mixture in a distillation step leaving acetic acid of lower water content. The acetic acid of lower water content may then be recycled to the reaction medium in the oxidation step.

According to a further form of the invention, at least part of the first aqueous medium and reaction medium removed through the band in the second zone optionally together with at least part of the reaction medium recovered from the first zone is returned to the oxidation step and/or distilled, eg added to said mixture distilled as mentioned above.

The so removed first aqueous medium and reaction medium and optionally the reaction medium recovered from the first zone are recycled indirectly, for example after evaporation to separate water and acetic acid from involatile materials, or preferably directly, to the oxidation step.

Standing concentrations of impurities in the process may be controlled by means of a purge for example by removal of at least some of the involatile materials recovered after evaporation.

The water and acetic acid separated in evaporation is preferably distilled optionally together with water and acetic acid of the stream removed from the oxidation step by evaporation, to produce acetic acid having a lower water content. Acetic acid having a lower water content may be passed to the oxidation step and the water recovered in distillation may be used as the first and/or second aqueous medium. Optionally at least part of the water recovered in distillation is used in other steps of the process and, if present in a purification plant.

The improved washing procedure of the invention permits higher impurity levels in the reaction medium in the oxidation step thus permitting the recycling of reaction medium from the first zone and/or the first aqueous medium and reaction medium from the second zone and consequently, a reduced purge is possible. A reduced purge is advantageous as desired materials, for example terephthalic acid, terephthalic acid precursor compounds and catalyst residues my be retained in the process.

The improved wash allows a slurry of terephthalic acid in the second aqueous medium having a lower level of impurities for example catalyst residues to be produced. Desirably this slurry is fed to a purification plant and the efficiency of the purification plant may consequently be improved. The lower level of impurities in the slurry allows mother liquor recovered from the purification plant, for example from the precipitation of purified terephthalic acid product, to be recycled, hence reducing the purge amount of waste effluent to be treated whilst maintaining an acceptable level of product purity. Furthermore, the recycled mother liquor may be used, optionally after further treatment for example cooling, filtering, distillation and/or evaporation, to wash the first wet deposit in the second zone. This allows a reduction in the amount of fresh water required for a given rate of wash or substantial elimination of fresh water intake.

The removal of the requirement for a separate drying stage and the expensive equipment required for it and the associated solids handling and storage provides a significant economic advantage in that capital costs may be reduced.

The band is suitably a metal gauze, or a cloth comprising a plastics material eg formed from polyester or polypropylene fibres. The band is suitably a continuous band which is moved continuously or intermittently to convey material comprising terephthalic acid from the first zone to the third zone through the second zone. The second zone suitably comprises a succession of stages in which, in each stage (other than the last), the incoming aqueous medium passed through the solids and the band is the aqueous medium which has passed through the solids and the band in the succeeding stage. In the last stage the aqueous medium is preferably fresh incoming water. This fresh incoming water is suitably at least in part water separated from acetic acid in the aforesaid distillation and/or evaporation stage or derived from other water streams within the process. This is advantageous as it reduces further the intake of fresh water and disposal of water in the process.

In the third zone the deposit may be scraped off the band, but it is preferably washed off with an aqueous medium, preferably substantially pure water, which may be in the form of jets of liquid at the end of the band. In the case of a continuous band, it is desirable to provide suitable means to pass liquid for example water or alkaline solution, through the returning part of the band to wash off downwardly facing adhering deposits into a receiver.

Desirably, there is a pressure differential across the moveable band, with the side of the band on which the slurry is deposited being at a higher pressure than the other side of the band. Suitably the differential pressure is at least 0.05 bar absolute and no more than the pressure at which the oxidation step is carried out, for example 30 bars absolute. Preferably the pressure differential is 0.1 to 15 bars absolute, more preferably, 0.2 to 7 bars absolute and especially 0.3 to 3 bars absolute, for example 0.6 bar absolute. The actual pressure on the lower pressure side of the band is maintained at such a pressure that the reaction medium and the aqueous medium removed through the band in the second zone remain substantially in the liquid phase.

Suitably the higher pressure side of the band is at substantially the same pressure or a higher pressure than the preceding step in the process, for example a crystallisation step or the oxidation step.

The slurry of terephthalic acid in acetic acid is suitably deposited on the moveable band at a temperature of at least 60° C. and preferably 70° to 200° C., especially 80° to 150° C. Suitably the slurry is deposited at a temperature which is sufficiently high that the pressure on the lower pressure side of the band is not less than 1 bar absolute.

Deposition of the slurry at elevated temperature is advantageous as improved filtration is possible due to the reaction medium being less viscous at elevated temperature. Furthermore there is less co-crystallisation of impurities for example 4-carboxybenzaldehyde, with the terephthalic acid product at elevated temperature. Thus a higher purity crude terephthalic acid product is obtained and there is a correspondingly higher level of impurities for example 4-carboxybenzaldehyde in the reaction medium. This allows re-optimisation of oxidation step reaction conditions such that variable costs may be reduced.

The elevated temperature may also improve heat recovery and hence provide a further reduction in variable costs. Furthermore, if a purification stage is employed, the slurry of terephthalic acid in the second aqueous is typically heated to dissolve the terephthalic acid; filtration at elevated temperature provides a slurry of terephthalic acid at elevated temperature therefore the amount of energy required to subsequently heat the slurry to dissolve the terephthalic acid is reduced.

The other individual steps of the process can be carried out conventionally. The liquid reaction medium normally comprises a catalyst, for example a cobalt/manganese/bromide catalyst system which is soluble in the reaction medium. Suitably the oxidation is carried out in the presence of an oxygen source for example air, at a pressure of 5 to 30 bars absolute, and preferably an oxygen concentration of 0 to 8% by volume in the gas leaving the reactor and at a temperature of 150° to 250° C. It is suitably a continuous process, and is preferably carried out in a stirred reactor. The reaction is exothermic and the heat of the reaction may conveniently be removed by evaporation of water and acetic acid from the reaction medium.

Suitably the slurry of the terephthalic acid product in the second aqueous medium is purified by a process which comprises dissolving the terephthalic acid in the second aqueous medium to produce a solution comprising terephthalic acid, contacting, under reducing conditions, the said solution with hydrogen and a heterogeneous catalyst for the reduction of at least some impurities, cooling the solution to precipitate solid purified terephthalic acid product and recovering the said product from the solution.

Suitably the heterogeneous catalyst employed in the purification of the crude terephthalic acid product may be a supported noble metal catalyst, for example platinum and/or preferably palladium on an inert, for example carbon, support. The reduction is suitably carried out by passing the aqueous solution comprising terephthalic acid and impurities, for example 4-carboxybenzaldehyde, through a flooded bed of catalyst as a temperature of 250° to 350° C. in the presence of hydrogen. The solution suitably comprises 20 to 50% by weight of terephthalic acid.

The solution after reduction is suitably cooled to a temperature in the range 100° to 250° C. to separate pure terephthalic acid product from the solution. This solution is preferably subsequently cooled to a temperature in the range 15° C. to 100° C. or evaporated to produce a less pure precipitate and a mother liquor. The less pure precipitate is suitably separated from the mother liquor. The mother liquor from this separation my be recycled directly or indirectly to distillation and/or be used as the second aqueous medium to reslurry the crude terephthalic acid. If desired the less pure precipitate may be recycled to the oxidation step.

Alternatively, if further purification is not employed, the terephthalic acid may be removed from the second aqueous medium, dried, for example by contacting it with a flow of inert gas. The dry terephthalic acid product may then used for further downstream processing. Optionally a crystallisation section may be employed to increase the yield of the terephthalic acid from the mixture of the second aqueous medium and terephthalic acid.

BRIEF DESCRIPTION OF THE DRAWINGS

One form of the invention will now be described with reference to the accompanying drawing, FIG. 1, which shows a flowsheet according to the invention and FIG. 2 which is a schematic representation of a filter and reslurry tank for use in the invention.

Reactor A is fed with paraxylene and acetic acid containing a dissolved catalyst comprising cobalt, manganese and bromine ions by line 1 and with air via line 2. Product from the reactor A is passed to crystallisation section B by line 3. The temperature within the reactor A is controlled by evaporating a mixture of acetic acid and water from the reactor to a condensing system C via line 4. Most of the condensate is returned to the reactor A via line 5 with noncondensibles venting via line 6. In order to control the water content of the reactor A, part of the condensate is removed from the condensing system via line 7 and passed to the distillation column D.

In the crystallisation section B the temperature is dropped to approximately 75° C. to 120° C. and the slurry containing crystalline terephthalic acid in mother liquor thereby produced is passed to filter stage E. Acetic acid may be recovered from crystallisation section B via streams 8 and 9 to the distillation column D and/or via streams 8 and 10 and/or 11 to the reactor A.

Figure 1:
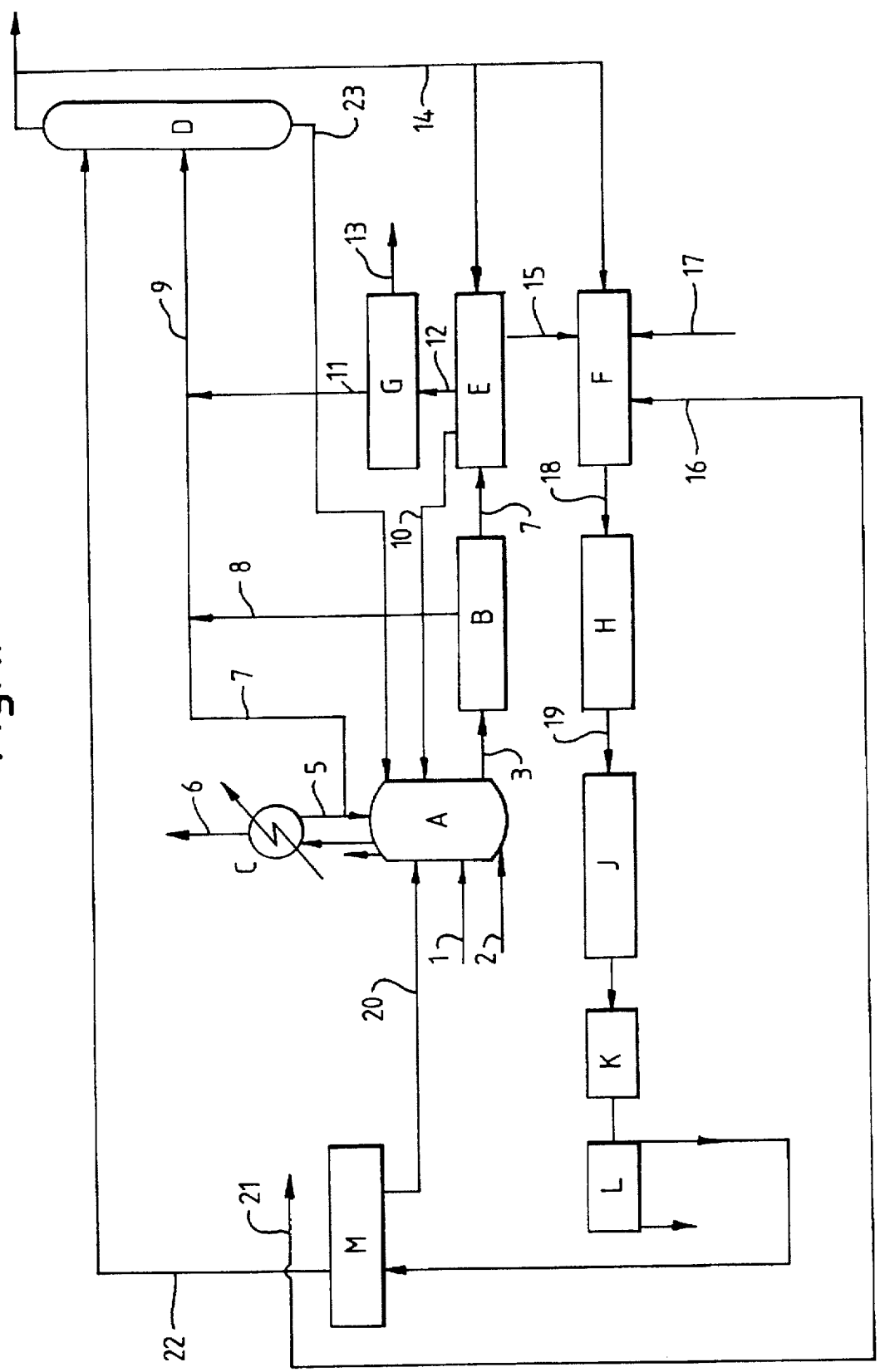
Figure 2:
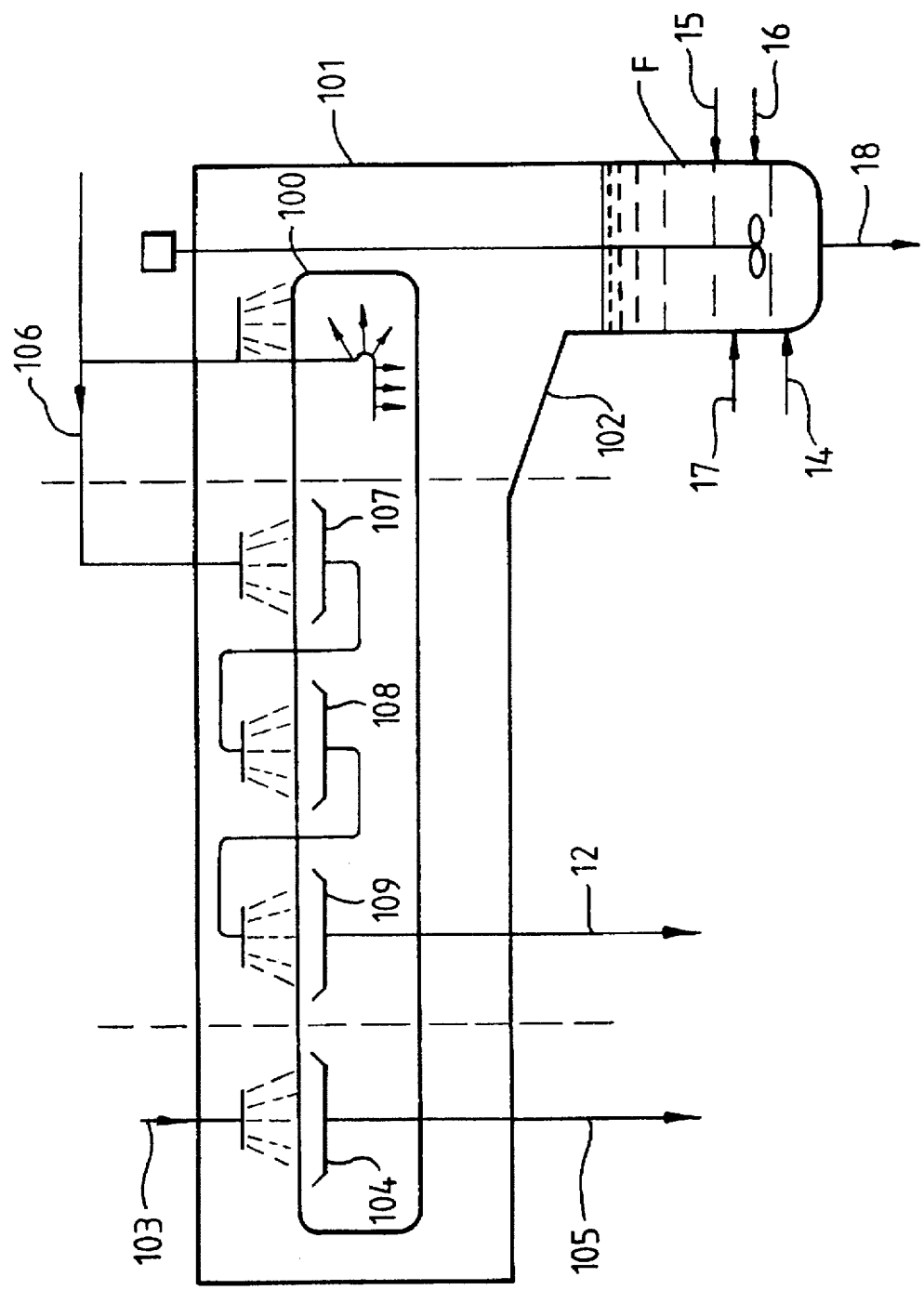

The filter stage E and reslurry tank F are shown in FIG. 2.

FIG. 2 shows a schematic representation of a continuous band filter E adapted for use in the invention, which comprises filter band 100 driven by rollers within the band (not shown) and enclosed in vapour tight housing 101 leading, by way of chute 102 to stirred reslurry tank F. Dotted lines show the locations of a first zone on the left in which a slurry of terephtalic acid and acetic acid together with any dissolved catalyst is introduced via line 103 onto the band and acetic acid drains through the band into collector pan 104 from which it is removed via line 105, a second (middle) zone in which water is introduced via line 106 and passed through the band three times to collector pans 107, 108 and 109 in turn thus washing deposits on the band with increasingly purer water as they pass each of the three washing stages provided thereby, and a third zone in which water is sprayed on and/or through the band to dislodge deposits on it into chute 102, leading to tank F, which may be fed with additional water if desired from lines 14, 15, 16 and/or 17. The water from line 106 may be derived from line 14, 15 or any other suitable source.

Mother liquor recovered from this stage is returned in part via line 10 to the reactor A optionally by first mixing with the fresh catalyst, paraxylene and acetic acid contained in line 1. Any remaining mother liquor and the wash liquid from the second zone is suitably passed to an evaporation stage G in which water and acetic acid vapour is removed by line 11, condensed and passed to reactor A or optionally passed to distillation column D and a purge of by products and catalyst is withdrawn via stream 13.

In reslurry vessel F the crystals are reslurried with water recovered from the distillation column D via stream 14 and/or other water which may be recycle mother liquor via stream 15, recycle mother liquor via stream 16 and demineralised water via stream 17.

The slurry produced in this stage is heated in section H to a temperature of for example 250° C. to 350° C. to form a solution which is passed via stream 19 to reactor J in which it is reacted with hydrogen over a fixed bed palladium catalyst thus reducing impurities in the solution and then again crystallised in crystallisation section K from which pure product is separated and dried in stage L which may comprise centrifuges and/or filters and a drier.

The temperature to which the solution is cooled in the crystallisation section K and the rapidity of cooling is adjusted to produce the appropriate purity of the desired terephthalic acid product. The pure terephthalic acid product is recovered from stage L and the mother liquor from the separation is passed to recovery stage M in which the liquid is evaporated or further cooled so as to permit the recovery of further solids which my be passed back to reactor A via stream 20. In stage M the temperature of the liquor may be reduced to 100° C. by flashing steam from it at atmospheric pressure. Such steam may be further purified for example by distillation and used if desired as wash in stage L, used elsewhere in the process or purged. The remaining liquor may be cooled or evaporated further and solids separated from it. The mother liquor recovered from stage M may be in part passed back to the distillation column D and processed as described later and may in part be returned to the reslurring stage F via stream 16 and may in part be purged via stream 21. Preferabling if evaporation is used the evaporated water is returned to the reslurry stage F.

The distillation column D fractionally distills a mixture of water and acetic acid evaporated from the reaction medium and is modified if required for use for the treatment of mother liquor separated from stage M.

The column D comprises three zones; the upper Zone 1 comprises for example 5 theoretical stages, the middle Zone 2 comprises for example 45 theoretical stages and the lower Zone 3 comprises for example 5 theoretical stages.

Part of the mixture of acetic acid and water evaporated from the reaction stage of oxidising p-xylene to terephthalic acid in reactor A is passed via stream 7 optionally together with stream 11 via line 9 to between the middle and lower zones of the column D. Mother liquor from the precipitation of terephthalic acid may be passed into the column D between the upper and middle zones via stream 22. Acetic acid and heavy material are passed from the base of the column D via stream 23 to reactor A. Water is condensed in the condenser and may be re-used in the process via stream 14.

The invention will now be illustrated by the following non-limiting examples.

EXAMPLE 1

Samples of crude terephthalic acid in reaction medium (crude slurry) were obtained from a commercial scale oxidation plant. The samples were filtered by a procedure which simulates a stage-wise counter current washing and filtration process.

A sample of crude slurry was filtered at 80° C. through a Buchner flask through which a vacuum was drawn using a filter cloth which was clamped across a supporting grid and arranged over the Buchner flask. A cylindrical vessel was clamped over the filter cloth to act as a reservoir for the sample and to retain the deposit of solids material.

The sample was washed with demineralised water and the filtrate was labelled F1(i). The deposit was discarded. A second sample was filtered and washed with F1(i) and the filtrate obtained was labelled F2(i). The sample was then washed with demineralised water and this filtrate was labelled F1(ii). The deposit was discarded. This procedure was repeated with a new sample wherein washing with F2(i) provided filtrate F3(i), washing with F1(ii) provided filtrate F2(ii) and washing with demineralised water provided F1(iii). The deposit was discarded.

A new sample was washed successively with with F3(i) (which provided filtrate F4(i) which was discarded), F2(ii) (which provided filtrate F3(ii)), F1(iii) (which provided filtrate F2(iii)) and demineralised water (which provided filtrate F1(iv)). This final washed deposit was analysed to determine the level of cobalt and manganese catalyst residues in it. By comparison with the known level of those residues in the sample slurry it was possible to determine the efficiency of the washing procedure.

Filtrate F4 represented the final wash filtrate in a 4 stage counter-current wash. Once the filtrates representing the filtrates obtained from the first (F1), second (F2), third (F3) and fourth (F4) stages of a 4 stage counter-current wash process had been generated they were used to wash a new sample and thereby produced filtrates F1–4 for the next wash cycle.

The washing procedure was repeated with a fresh sample until the level of impurities in deposits obtained from successive wash cycles remained substantially constant The results are shown in Table 1.

EXAMPLE 2

The procedure of Example 1 was repeated to simulate a 3 stage counter-current wash procedure, that is, the filtrate labelled F3 was discarded and the deposit obtained in the production of F3 was analysed to determine levels of cobalt and manganese residues.

The results are shown in Table 1.

EXAMPLE 3 (COMPARATIVE)

A conventional washing and drying procedure, not according to the invention, was employed. Samples of crude terephthalic acid in reaction medium (crude slurry) identical in composition to those used in Examples 1 and 2 (obtained from the same source at the same time) were filtered using a commercially available vacuum filter and washed with acetic acid. The samples were dried using a commercially available vacuum steam tube drier. The dried deposits were analysed to determine the level of cobalt and manganese in them according to the same method as that employed in Examples 1 and 2. The filtration and washing was carried out at 80° C. and at the same differential pressure as the washings in Examples 1 and 2.

The results are shown in Table 1.

TABLE 1

| | Wash Rate (te/te deposit) | Cobalt (ppm) | Removal (weight %) | Manganese (ppm) | Removal (weight %) |
|---|---|---|---|---|---|
| Example 1 | 0.30 (water) | 0.3 | 99.90 | 2.1 | 99.65 |
| Example 2 | 0.21 (water) | 0.5 | 99.85 | 3.0 | 99.50 |
| Example 3 (Comparative) | 0.21 (acetic acid) | 7.0 | 96.6 | 25.0 | 96.6 |

These results illustrate that a process according to the invention has an improved wash efficiency as compared with a conventional prior art washing process.

We claim:

1. In a process for the preparation of terephthalic acid comprising oxidising paraxylene in a reaction medium comprising acetic acid to produce a slurry of crude terephthalic acid in acetic acid-based mother liquor, separating the crude terephthalic acid from the acetic acid-based mother liquor, dissolving the crude terephthalic acid in water to produce an aqueous solution of crude terephthalic acid, purifying the terephthalic acid by contacting the aqueous solution with hydrogen and a heterogeneous catalyst, and separating the purified terephthalic acid from the aqueous mother liquor, the improvement wherein:

separation of the crude terephthalic acid from the acetic acid-based mother liquor is effected by means of an integrated separation and multistage countercurrent washing filter operation under elevated temperature conditions; and said integrated separation and countercurrent washing filter serves initially to filter the acetic acid-based mother liquor from the crude terephthalic acid and then replace residual acetic acid-based mother liquor with water-based wash liquor including aqueous mother liquor separated from the purified terephthalic acid.

2. A process as claimed in claim 1 in which the aqueous mother liquor employed as wash liquor in said countercurrent washing filter is supplied to said filter in untreated form.

3. A process as claimed in claim 1 in which the aqueous mother liquor employed as wash liquor in said countercurrent washing filter is supplied to said filter in treated form.

4. A process as claimed in claim 3 in which treatment of said aqueous mother liquor comprises cooling thereof following separation from the purified terephthalic acid.

5. A process as claimed in claim 4 in which further less pure terephthalic acid is precipitated from the aqueous mother liquor on cooling and said less pure precipitate is supplied to the oxidation reaction.

6. A process as claimed in claim 3 in which treatment of said aqueous mother liquor comprises distillation thereof.

7. A process as claimed in claim 6 further comprising controlling the temperature of the oxidation reaction by withdrawing as vapour a mixture of acetic acid and water from the reaction, removing water from at least part of the mixture in a distillation column leaving acetic acid of lower water content, and returning acetic acid from the distillation column to the reaction, said treatment of the aqueous mother liquor being effected in said distillation column.

8. A process as claimed in claim 7 in which treatment of said aqueous mother liquor comprises cooling thereof with accompanying precipitation of less pure terephthalic acid, followed by distillation of the cooled mother liquor, said less pure precipitate being supplied to the oxidation reaction.

9. A process as claimed in claim 8 in which said integrated separation and countercurrent washing filter comprises a band of filter material.

10. A process as claimed in claim 8 in which said integrated separation and countercurrent washing filter comprises a continuous band of filter material.

11. A process for the production of terephthalic acid comprising:

supplying to a first reaction zone paraxylene, acetic acid, a dissolved catalyst comprising cobalt, manganese and bromine ions, and oxygen to effect oxidation of paraxylene to terephthalic acid;

controlling the temperature of the reaction by withdrawing from the reaction zone as vapour a stream of acetic acid and water;

supplying part of the acetic acid and water withdrawn from the reaction zone to a distillation zone and separating water from acetic acid in said distillation zone;

returning the acetic acid so separated to the reaction zone;

withdrawing from the reaction zone a crude slurry of crude terephthalic acid in acetic acid-based mother liquor;

providing an integrated separation and countercurrent washing filter zone supplied with water-based washing liquor and filtering the crude terephthalic acid from the acetic acid-based mother liquor in said filter zone to form a filter cake and replacing residual acetic acid-based mother liquor in the filter case with water-based liquor;

dissolving the washed crude terephthalic acid in water to produce an aqueous solution of crude terephthalic acid;

purifying the crude terephthalic acid in a second reaction zone by contacting the aqueous solution of crude terephthalic acid with hydrogen and a heterogeneous catalyst to effect reduction of impurities associated with the crude terephthalic acid;

separating the purified terephthalic acid from water-based mother liquor; and feeding water-based mother liquor so separated to said integrated separation and countercurrent washing filter for use as said water-based liquor.

12. Process as claimed in claim 11 which includes the step of feeding water derived from the distillation column to said filter zone as water-based liquor.

13. Process as claimed in claim 12 in which the integrated separation and countercurrent washing filter zone comprises a filter band on which the separation and washing steps are carried out.

14. Process as claimed in claim 13 in which the filter band is continuous.

15. Process as claimed in claim 14 in which the filter band comprises a plastics material.

* * * * *